United States Patent [19]

Lutenegger et al.

[11] 4,122,704
[45] Oct. 31, 1978

[54] PORTABLE VARIABLE EXPANSION TESTING DEVICE FOR MEASURING LATERAL PRESSURE INDUCED ON A MATERIAL BY A VERTICAL APPLIED PRESSURE

[75] Inventors: Alan J. Lutenegger; Richard L. Handy; James M. Hoover, Ames, Ala.L OF IA

[73] Assignee: Iowa State University Research Foundation, Ames, all of Iowa

[21] Appl. No.: 836,153

[22] Filed: Sep. 23, 1978

[51] Int. Cl.² ............................................. G01N 3/10
[52] U.S. Cl. ........................................ 73/822; 73/825
[58] Field of Search ...................... 73/94, 432 R, 88 E

[56] References Cited

U.S. PATENT DOCUMENTS

| 1,998,722 | 4/1935 | Hveem ................................... 73/94 |
| 3,779,085 | 12/1973 | Rice .................................... 73/432 R |
| 4,047,425 | 9/1977 | Handy et al. ............................ 73/94 |

FOREIGN PATENT DOCUMENTS 862,376  11/1952  Fed. Rep. of Germany .......... 73/88 E Primary Examiner—Anthony V. Ciartante
Attorney, Agent, or Firm—Zarley, McKee, Thomte, Voorhees & Sease

[57] ABSTRACT

A portable testing device for directly measuring developed lateral pressure induced on a material by a vertical applied pressure while the lateral expansion is adjustable. The testing device comprises a thin-walled cylindrical sleeve-like receptacle which is capable of lateral expansion in response to a vertical applied force on the material contained in the receptacle. The sleeve is provided with a slit formed in the wall thereof which extends between the upper and lower ends thereof to define first and second side edge portions. Apparatus is provided for preventing and/or adjusting lateral movement of the first side edge portion as the vertical applied force is applied to the material contained in the receptacle. A pressure sensing cylinder is connected to the second side edge portion and has a fluid pressure gauge operatively connected thereto for sensing the developed lateral stress.

13 Claims, 9 Drawing Figures

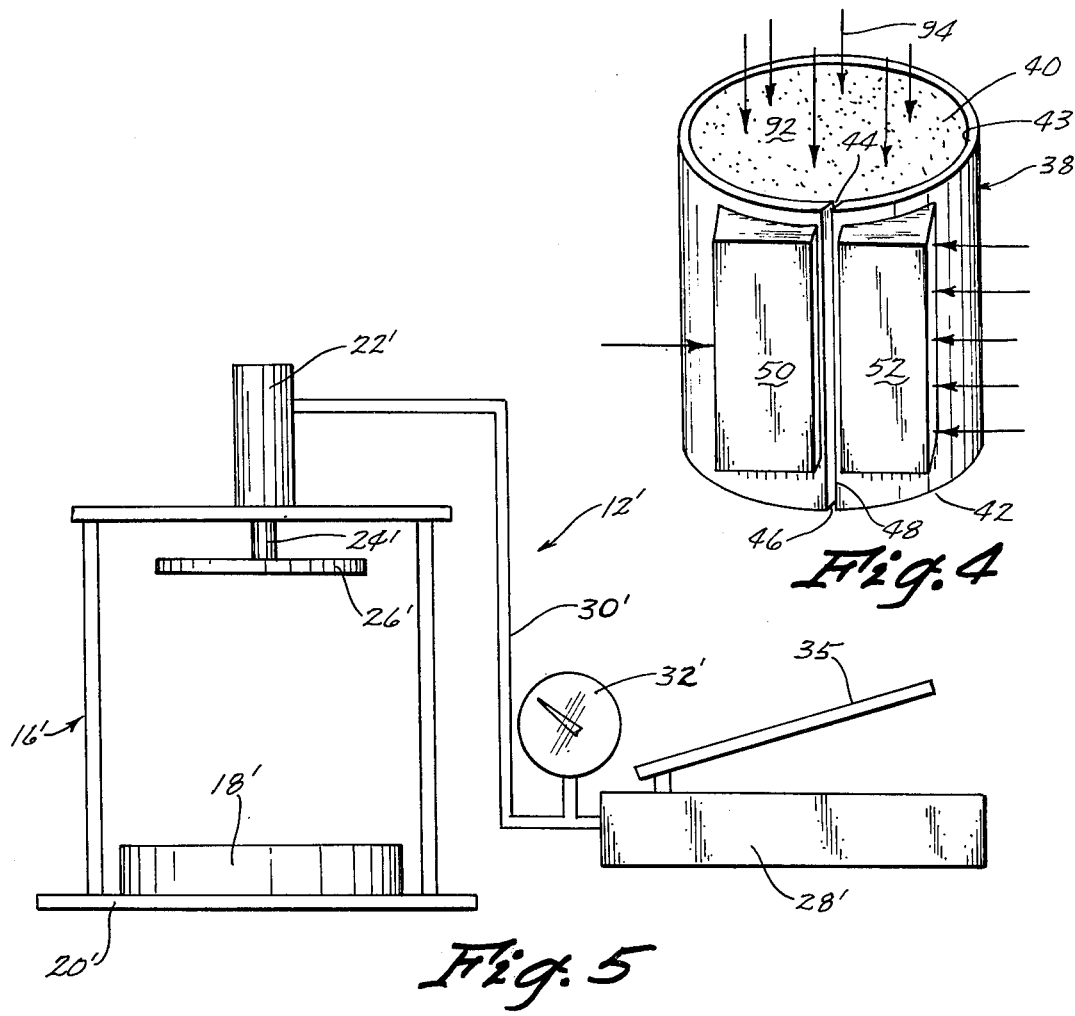
Fig. 4
Fig. 5
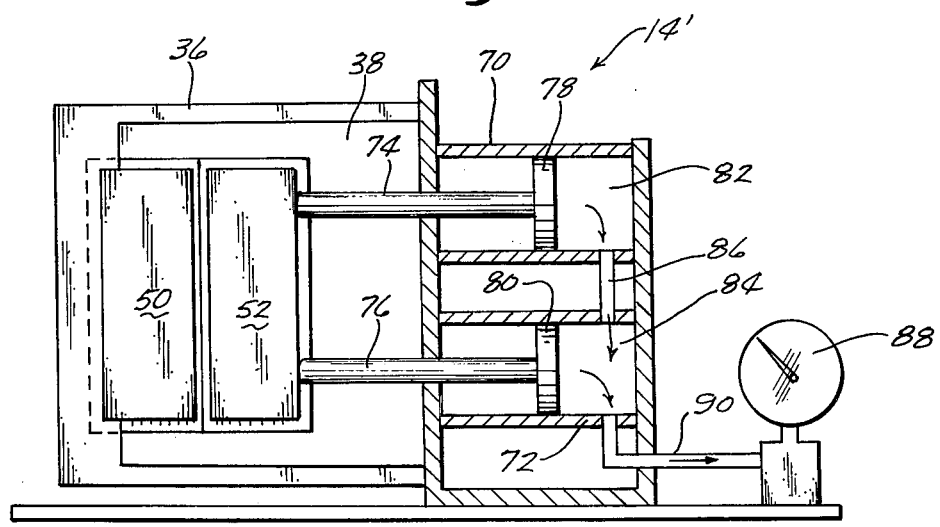
Fig. 6

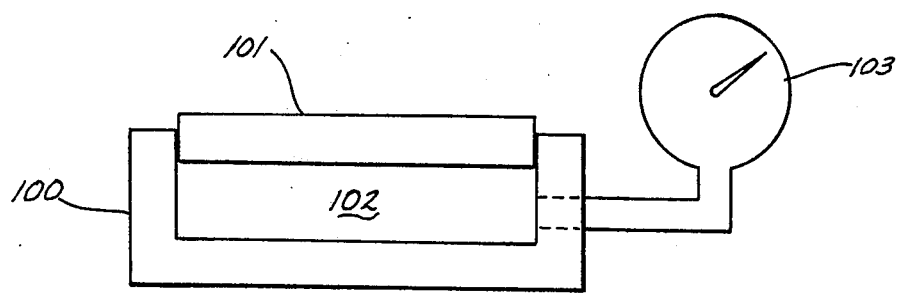
Fig. 7
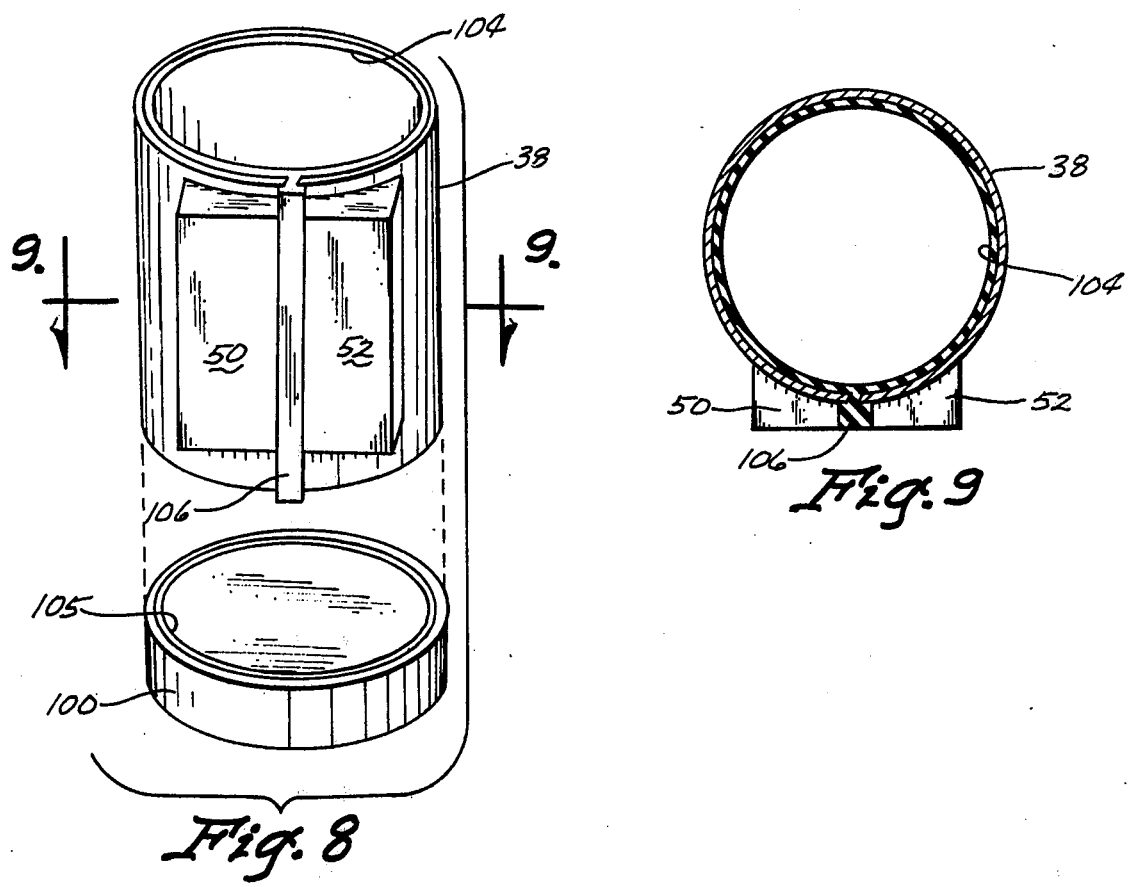
Fig. 8
Fig. 9

PORTABLE VARIABLE EXPANSION TESTING DEVICE FOR MEASURING LATERAL PRESSURE INDUCED ON A MATERIAL BY A VERTICAL APPLIED PRESSURE

BACKGROUND OF THE INVENTION

The lateral pressure induced upon soil under a vertical applied pressure is an important and fundamental aspect of engineering behavior of the soil particularly in relationship to the pressure on retaining walls and to the soil-bearing capacity under loads. For example, assuming that the lateral pressure for a particular soil equals one-half of the vertical pressure; a vertical loading of 100 p.s.i. will cause a lateral pressure of 50 p.s.i. on an adjacent retaining wall, the ratio of lateral to vertical pressure in this case being one-half. Thus, the adjacent retaining wall must be able, at a minimum, to withstand a lateral pressure equal to one-half the vertical stress from the weight of the soil, which of course increases with depth. The relationship to bearing capacity of a given soil is somewhat more complicated than the above example since the lateral pressure tends to cause adjacent underlying soil to be displaced laterally which can induce a bearing capacity failure or what is termed "rutting". This is true because, when the adjacent soil is displaced laterally, soil adjacent to the laterally displaced soil develops its own minor principal stress as an uplift pressure that may exceed the restraining weight of the adjacent overburden soil.

As one can see, the importance of monitoring the ratio of lateral stress to vertical stress is of critical importance for placing any structure upon the soil. It is therefore of value to assess this relationship and to evaluate its effect for a given soil sample in order to know whether or not the soil can properly withstand the applied vertical pressure. The ratio of lateral to vertical stress is known as the Rankine stress ratio and is termed "K".

It is an object of this invention to provide a soil testing device which can continually monitor the Rankine stress ratio on a soil sample, as vertical pressure is increased, in order to determine the lateral stresses induced by a given vertical applied pressure in adjacent soil.

An additional object of this invention is to provide means for monitoring and adjusting lateral restraint on the sample, in order to more closely simulate field behavior of soil surrounded by identical soil.

An additional object of this invention is to provide a Rankine stress monitoring device which may be used either on undisturbed field samples or soil samples which have been subjected to pre-treatment in order to simulate anticipated environmental conditions.

Still another object of this invention is to provide a continuous K testing device which can be utilized to test soil having been subjected to all sorts of environmental conditions such as freezing, thawing, snow, water soaking, or other conditions.

Yet another object of this invention is to monitor the Rankine stress ratio during a program of cyclical loading and unloading designed to simulate soil stress conditions that are known to occur in soils as a result of vehicular traffic or earthquakes.

One device of the prior art utilizes a stress gauge to sense the amount of lateral displacement of the receptacle. However, the device of instant invention permits direct measurement of developed lateral stress as well as direct measurement of applied vertical stress through fluid pressure. The testing device of this invention permits field conditions to be ideally simulated since the lateral elasticity is governed by compression of fluid so as to increase in magnitude as the test progresses.

A further object of the invention is to provide a testing device which is portable so that the test may be conducted at a field site on samples obtained therefrom.

A further object of the invension is to provide a testing device that directly measures the soil-to-steel coefficient of sliding friction.

BRIEF DESCRIPTION OF THE DRAWINGS

This invention consists in the construction, arrangements and combination of the various parts of the device, whereby the objects contemplated are attained as hereinafter more fully set forth, specifically pointed out in the claims, and illustrated in the accompanying drawings in which:

FIG. 4 is a perspective view of the material holding receptacle.

FIG. 5 is a side view of a modified form of a loading mechanism.

FIG. 6 is a partial schematic side view of a modified form of the lateral pressure measuring apparatus.

FIG. 7 is a side view of the alternate base measuring device for use in obtaining soil-to-steel coefficient of friction.

FIG. 8 is a perspective view of the seals utilized in the material holding receptacle for preventing water escape from the material.

FIG. 9 is a top plan view of FIG. 8.

DETAILED DESCRIPTION OF THE INVENTION

Figure 1:
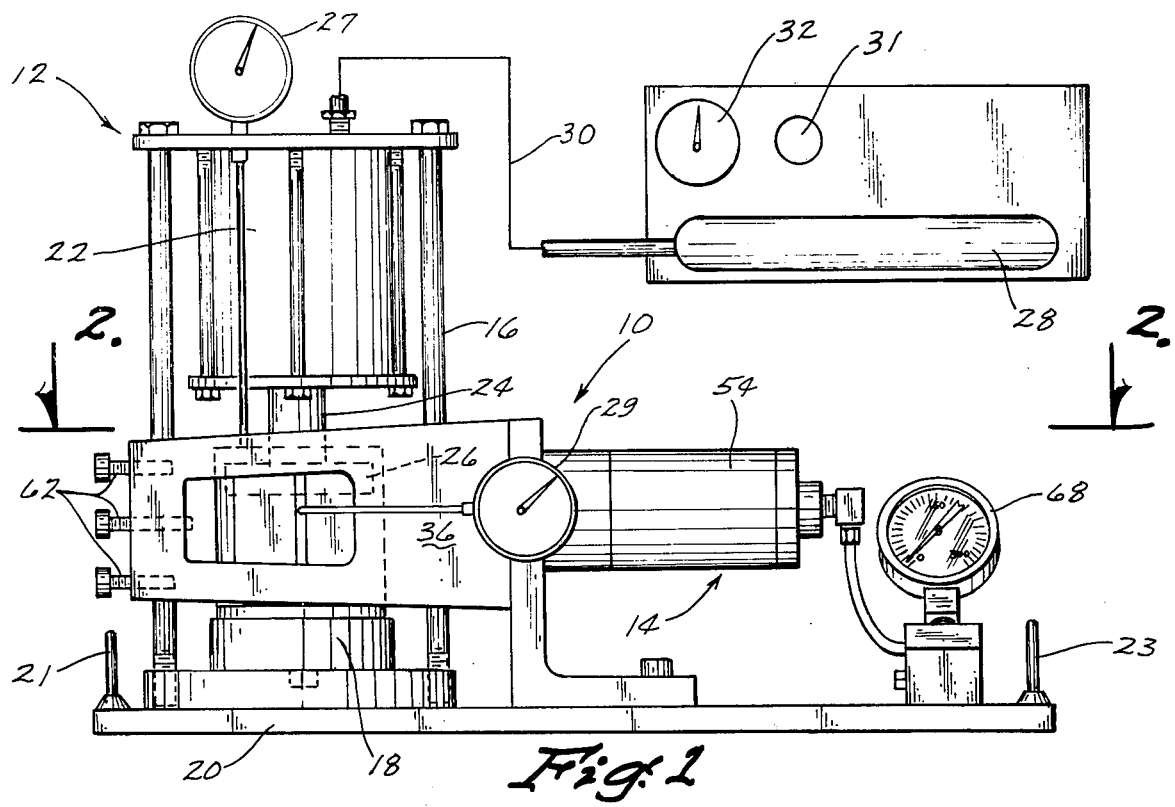
FIG. 1 is a side view of the testing device of this invention.
Figure 2:
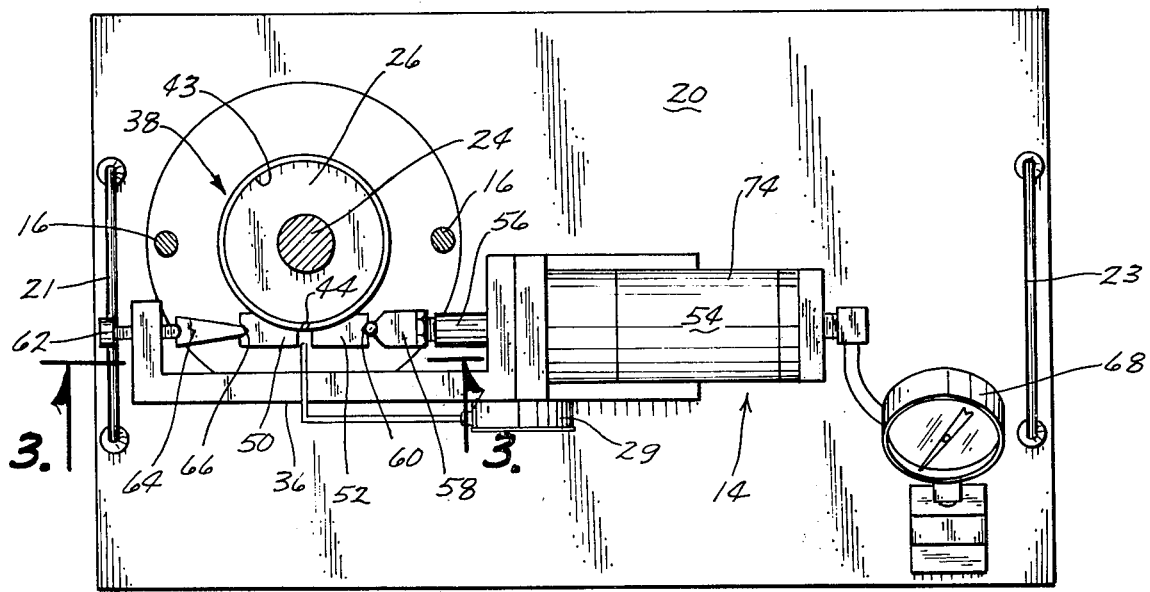
FIG. 2 is a sectional view of the device as seen on lines 2—2 of FIG. 1.

The portable testing device of this invention, as distinguished from certain other testing devices, has the advantage of being able to test soil samples that have no cohesion since, in the device of this invention, the soil is confined wholly within the device thereby avoiding the need for cohesive samples.

The continuous Rankine stress monitoring device 10 of FIGS. 1-4 generally comprises a loading mechanism 12 and a lateral pressure measuring system 14 mounted on the base 20 having handles 21 and 23 secured thereto. Mechanism 12 generally comprises a load frame 16 having a plate 18 positioned on the base 20 thereof. A loading cylinder 22 is positioned on the upper end of the load frame 16 and has a cylinder rod 24 extending downwardly therefrom which has a plate 26 secured to the lower end thereof. Dial gauge 27 measures vertical deflection while dial gauge 29 measures horizontal expansion. The interior of cylinder 22 is fluidly connected to pressurized container of carbon dioxide 28 by line 30. The apparatus also includes a pressure regulator 31 and pressure gauge 32. Thus, operation of the container 28 causes pressure to be supplied to the cylinder 22 thereby extending or lowering the cylinder rod 24.

A simplified or modified form of the loading mechanism is illustrated in FIG. 5 by the reference numeral 12'. Mechanism 12' includes a load frame 16' having a plate 18' positioned on the base 20'. Loading cylinder 22' is mounted on the upper end of load frame 16' and has a cylinder rod 24' extending downwardly therefrom which has a plate 26' secured to the lower end thereof. The interior of cylinder 22' is fluidly connected to a manually operated hydraulic pump 28' by line 30'. Pressure gauge 32' is fluidly connected to the line 30' as illustrated. Thus, manual operation of the foot pedal 35 causes fluid to be supplied to the cylinder 22' to extend or lower the cylinder rod 24' and plate 26'.

The lateral pressure measuring system 14 of FIGS. 1–4 generally comprises a holding bracket 36 designed to support the cylindrical receptacle 38. Receptacle 38 has an open top end 40 and an open bottom end 42. Receptacle 38 has a slit 44 along its entire length parallel to the longitudinal axis of the cylindrical receptacle 38, which is sometimes referred to hereinafter as a cylindrical sleeve. Slit 44 defines side edge portions 46 and 48 as illustrated in FIG. 4. Blocks 50 and 52 are secured to the exterior surface of the receptacle 38 adjacent side edge portions 46 and 48 respectively.

Figure 3:
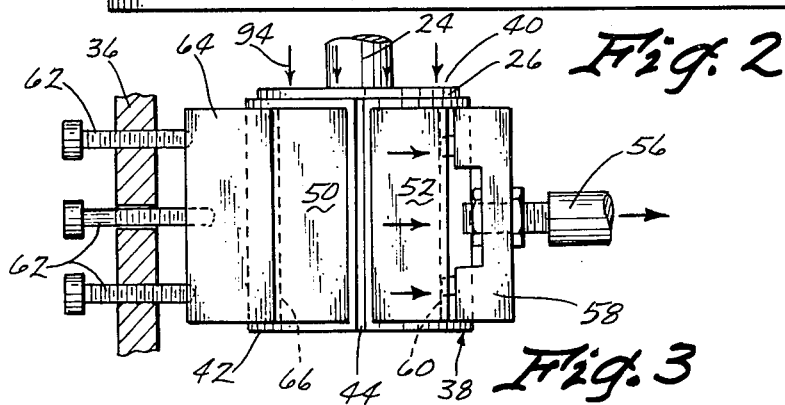
FIG. 3 is a sectional view as seen on lines 3—3 of FIG. 2.

A lateral pressure cylinder 54 is mounted on the holding bracket 36 in the manner illustrated in FIG. 1 and has cylinder rod extending from the piston thereof. Rod 56 has an adapter 58 on its outer end adapted to engage groove 60 on block 52. Adjustment screws 62 extend through bracket 36 as best seen in FIG. 3 and have an adapter 64 mounted on the inner ends thereof for engagement with groove 66 in block 50. The cylinder 54 is provided with a fluid compartment therein at one side of the piston contained therein. The fluid compartment is in fluid communication with a pressure gauge 68. Thus, movement of the block 52 towards the pressure cylinder 54 will cause the fluid in the compartment in the cylinder 54 to be compressed thereby causing the increased pressure therein to be registered on the gauge 68.

The modified lateral pressure monitoring system of FIG. 6 is generally referred to by the reference numeral 14' and is quite similar to the system 14 except that a pair of lateral pressure cylinders 70 and 72 are utilized.

Cylinders 70 and 72 have cylinder rods 74 and 76 extending from the pistons 78 and 80 respectively. Rods 74 and 76 are in an abutting relationship with block 52 as seen in FIG. 6. The cylinders 70 and 72 have fluid compartments 82 and 84 at one side of the pistons contained therein. Fluid compartments 82 and 84 are in fluid communication with each other, by means of line 86, and with a pressure gauge 88 by means of line 90.

Base pressure cell 100 in FIG. 7 has loading cap 101 which is in contact with the soil sample 92 during testing. Material receptacle 38 rests on base 100 during loading. Fluid compartment 102 is in fluid communication with pressure gauge 103.

Water seals 104 and 105 are in contact with plate 26 and plate 18 respectively. These maintain sample pore fluid within receptacle ends 40 and 42 while sample is being loaded. In addition, seal 106 is placed between blocks 50 and 52, and covers slit 44 to prevent leakage along the split.

In actual operation, the continuous K testing device works as follows. A soil sample 92 is placed within cylindrical receptacle 38 with, of course, plate 18 being received by the lower open end of the receptacle 38. A top closure member is placed within cylindrical sleeve 38 directly on top of soil sample 92. A vertical applied pressure, as indicated by arrows 94, is applied downwardly against the top closure member and correspondingly on soil sample 92 by the loading mechanism 12 or 12'. The vertical applied pressure in the direction of arrows 94 causes an induced lateral pressure on the soil sample 92 and correspondingly on the lateral wall surface of the cylindrical sleeve 38. The induced lateral pressure causes expansion of sleeve 38 transverse to its longitudinal axis with the result being that the width of the slit 44 is increased. As previously stated, block 50 is prevented from lateral movement by means of the holding bracket 36 and screws 62 so that edge portion 48 moves laterally with respect to edge portion 46 as the width of the slit 44 increases. Lateral movement of edge portion 48 causes compression of the fluid in the compartment in cylinder 54 which is registered on the pressure gauge 68 to provide a reading thereon when the embodiment of FIGS. 1–4 is being employed. When the embodiment of FIG. 6 is being employed, lateral movement of edge portion 48 causes compression of the fluid in the compartments 82 and 84 which is registered on the pressure gauge 88.

By application of a series of predetermined vertical pressures and monitoring of the corresponding developed lateral pressures through the gauges 68 or 88, one obtains a continuous response record for a particular soil, such that the developed lateral pressure is predicted for any anticipated level of vertical pressure. The apparatus of the invention provides a direct measurement of developed lateral stress and applied vertical stress through fluid pressure. As the soil specimen is compressed vertically in the receptacle 38, developed lateral stresses create a fluid pressure which is read directly from the pressure gauges 68 or 88. Since the lateral elasticity is now governed by compression of the fluid, it increases in magnitude as the test progresses. This results in an ideally simulated field condition where the in-situ adjacent soil may change properties during loading.

For measurement of soil-to-steel coefficient of sliding friction, plate 18 is replaced by cell 100. With receptacle 38 resting on cell 100 all frictional resistance is directed upward. During testing, when a top vertical pressure is applied a bottom vertical pressure is recorded on gauge 103. Subtracting bottom pressure from top pressure gives amount of stress attributed to side friction on receptacle 38. As the lateral stress is also known, through mathematical calculations, the coefficient of soil-to-steel friction is obtained.

Also during loading, seals 104, 105 and 106 prevent leakage of water giving the shear strength parameters on an undrained basis.

The Rankine lateral stress ratio is continuously monitored and the portability of the instant invention permits tests to be conducted at a field site on samples obtained therefrom. This is advantageous for control of compacted fills for embankments or filled placement behind retaining structures. Shear strength can now be evaluated on site.

The cylindrical receptacle 38 provides minimal lateral restraint with the majority of restraint provided by the amount of fluid in monitoring device 10. In a field loading situation this intensity of lateral confinement varies depending on the soil. A measure of confining soil stiffness is its modulus of elasticity in p.s.i. For a realistic test the typical monitoring device 10 modulus, as measured in p.s.i., is the following for various types of soil samples.

| Soil | Mold Expansion Modulus, p.s.i. |
|---|---|
| Dense gravel, sand-gravel, crushed rock, sand | 18,000 – 20,000 |
| Loose sand, dense silt, clay | 4,000 – 6,000 |
| Soft silt, clay | 1,500 – 2,500 |

The stiffness also may be selected to simulate elastic behavior of a confining structure, as a retaining wall. For special purposes, such as comparisons of many soil samples, a constant stiffness may be preferred even though this does not represent a best simulation of field stress conditions. It should be noted that even in this case, the elastic behavior of the K-test is much closer to field conditions than is presented by conventional soil shear strength testing wherein the confining pressure is maintained at an arbitrary constant level which bears little or no relationship to actual stresses occurring in the field.

If desired, the mold interior wall surface 43 can be polished and chromeplated or lined with teflon to reduce friction and abrasion.

Certain other advantages for the structure of this invention are apparent from the very fact that the test is a continuous test which measures developed stresses rather than current engineering practices which measures maximum values.

For example, most soils have both internal friction $\phi$ and a cohesion intercept $c$, or shearing strength under zero applied normal stress. Mathematically, it can be shown that from a consideration of the changes in the Rankine stress ration, K, one may define by mathematical computation both cohesion $c$ and friction angle $\phi$ for an individual soil.

A particular advantage of the continuous K-test device is that it may be used with either undisturbed field samples or laboratory molded samples, and because of the confined nature of the test and mobility of the test mold practically any pre-treatment may be used which simulates an anticipated environment. This is in contrast to other tests where the lack of confinement may allow samples to fall apart. For example, K-test specimens may be saturated with water prior to testing. Not only does this impose an extreme environmental condition that frequently occurs in the field but valuable supplementary data may be obtained on expansive or collapsible character of the particular soil by measuring the specimen height before and after soaking. A realistic surcharge load also may be used during soaking to better simulate field conditions. Similarly, specimens may be dried to indicate shrinkage, or they may be frozen and thawed to indicate deleterious frost action, or they may be chemically treated to improve stability. No other test offers these potentials in quite so convenient and controllable a form, because practically all tests which provides $c$, $\phi$ and K data require the use of several different specimens.

By preventing escape of pore-water from the soil sample during testing, the undrained or worst condition is simulated. For example, undrained shear strength would be used for design in the case of an embankment constructed rapidly over a soft clay deposit or a strip loading placed rapidly on a clay deposit.

It can also be seen that an additional advantage of the structure of the K-test device of this invention is that the testing may be performed under slow or static loading conditions to give a behavior usually identified as soil creep. Alternatively, the test may be performed with a cyclical loading and unloading designed to simulate soil stress conditions that are known to occur in soils as a result of vehicular traffic or earthquakes.

As heretofore previously mentioned the directness of the soil test is an advantage compared with prior art tests since in use of the device of the present invention the developed K, $c$, $\phi$ and E unit strain are evaluated rather than the maximum or limiting values.

In current engineering practice, maxima are obtained and divided by an arbitrary number called a "factor of safety" to assure that the failure stress conditions are never reached. Since the limiting conditions are seldom reached simultaneously through a soil mass, most soil mechanics problems are theoretically indeterminate, i.e., the number of unknowns exceeds the number of variables and critical assumptions must be made for the analysis. These are all covered in the factor of safety. This is to be contrasted with the analysis which can be made utilizing the structure of the present invention wherein the design allows the actual measurement of a developed response rather than a determination of maximum responses. It is therefore much closer to actual environmental conditions.

Thus it can be seen that the invention accomplishes at least all of its stated objectives.

What is claimed is:

1. A testing device to measure the lateral pressure induced on a material by a vertical applied pressure, said testing device comprising in combination,
    a support means,
    a material holding receptacle operatively mounted on said support means which is capable of lateral expansion in response to a vertical applied force on a material contained in said receptacle,
    said receptacle being an elastic, cylindrical sleeve having a vertical slit along its entire length to define first and second vertical edge portions,
    means retaining said first vertical edge portion against lateral movement upon said vertical applied pressure being applied to said material in said sleeve,
    at least one lateral pressure cylinder means comprising a cylinder body having a movable piston therein, a cylinder rod connected to said piston and extending from said body and being operatively connected to said second vertical edge portion,
    and a fluid pressure gauge operatively connected to said cylinder body for sensing and indicating pressure created in said second vertical edge portion being laterally deflected with respect to said first vertical edge portion when said vertical applied pressure is applied to said material in said sleeve.

2. The device of claim 1 wherein said lateral pressure cylinder means comprises a generally closed hydraulic system whereby the pressure therein progressively increases in response to deflection of said second vertical edge portion with respect to said first vertical edge portion during lateral expansion of said receptacle.

3. The device of claim 2 wherein a pair of lateral pressure cylinders are mounted on said support means, in vertically spaced relation, said pair of cylinders being in fluid communication with each other whereby a combined resultant pressure is registered on said fluid pressure gauge.

4. The device of claim 2 including a base pressure cell interposed between said receptacle and said support means, said base pressure cell including a fluid compartment which is compressed in response to vertical applied pressure on said material, and a pressure gauge in fluid communication with said fluid compartment.

5. The device of claim 2 wherein a load device for creating said vertical applied pressure is operatively secured to said support means.

6. The device of claim 5 wherein said source of fluid pressure comprises a manually operated hydraulic pump.

7. The device of claim 5 wherein said load device comprises a support member having a vertically disposed pressure cylinder positioned over said sleeve and having a plate means mounted thereon for engagement with said material, and a source of fluid pressure operatively connected to said vertically disposed pressure cylinder.

8. The device of claim 7 wherein a fluid pressure gauge is operatively connected to said source of fluid pressure for indicating the fluid pressure applied to said material.

9. The device of claim 7 wherein said source of fluid pressure comprises a pressurized cannister means.

10. The device of claim 9 wherein a pressure regulator is operatively connected to said pressurized cannister means.

11. A testing device to measure the lateral pressure induced on a material by a vertical applied pressure, said testing device comprising in combination, a material holding receptacle which is capable of lateral expansion in response to a vertical applied force on a material contained in said receptacle, said receptacle having a vertically disposed slit along its entire length to define first and second vertically disposed edge portions, a generally closed fluid pressure system, means operatively connecting said fluid pressure system to said receptacle such that pressure in said system is increased in response to movement of said first edge portion with respect to said second edge portion during lateral expansion of said receptacle, and means for sensing the pressure within said fluid pressure system.

12. The device of claim 11 further comprising a portable support means, means for supporting said receptacle on said support means with said first edge portion secured against lateral movement, said fluid pressure system including a cylinder member and a piston member movably received therein, one of said members being secured to said portable frame and the other of said members being connected to said second edge portion for movement therewith.

13. The device of claim 12 including a portable load device operatively secured to said portable support means for creating said vertical applied pressure.

* * * * *